US012678231B2

(12) United States Patent
Wolfson et al.

(10) Patent No.:     US 12,678,231 B2
(45) Date of Patent:          Jul. 14, 2026

(54) SYSTEM AND METHODS FOR FEMUR-FIRST ORTHOPAEDIC SURGICAL PROCEDURES

(71) Applicant: DEPUY IRELAND UNLIMITED COMPANY, Ringaskiddy (IE)

(72) Inventors: David Wolfson, Batley (GB); Nicolas Demanget, Cambridge, MA (US); Sarah Radcliffe, Rawdon (GB); Daniel Girardeau-Montaut, Grenoble (FR)

(73) Assignee: DePuy Ireland Unlimited Company, Ringaskiddy (IE)

( * ) Notice: Subject to any disclaimer, the term of this patent is extended or adjusted under 35 U.S.C. 154(b) by 104 days.

(21) Appl. No.: 18/232,388

(22) Filed: Aug. 10, 2023

(65) Prior Publication Data

US 2025/0049505 A1     Feb. 13, 2025

(51) Int. Cl.
  *A61B 34/10*     (2016.01)
  *A61B 17/15*     (2006.01)
  *A61B 34/30*     (2016.01)
  *A61B 34/20*     (2016.01)

(52) U.S. Cl.
  CPC ............ *A61B 34/10* (2016.02); *A61B 17/155* (2013.01); *A61B 17/157* (2013.01); *A61B 34/30* (2016.02); *A61B 2034/2068* (2016.02)

(58) Field of Classification Search
  CPC . A61B 34/20; A61B 90/39; A61B 2090/3983; A61B 17/15; A61B 17/154; A61B 17/155; A61B 17/157
  See application file for complete search history.

(56) References Cited

U.S. PATENT DOCUMENTS

2015/0196308 A1*   7/2015  Wilkinson ........... A61B 17/157
                                                606/88

OTHER PUBLICATIONS

Conformis, Inc., iUni G2 Surgical Technique Guide, Patient-Specific Unicompartmental Knee Resurfacing System, Femur First, 2012, 24 pages.
Depuy Synthes, Velys Robotic-Assisted Solution for Total Knee, Surgical Technique, Femur First Approach, Version 1.3, 2021, 72 pages.
Depuy Synthes, "Intuition Instruments for HP Partial Unicondylar Knee Replacement, Surgical Technique," 2022, 36 pages.
Depuy Synthes, "Sigma High Performance Partial Knee, Unicondylar, Surgical Technique," 2020, 28 pages.
(Continued)

*Primary Examiner* — Samuel S Hanna
(74) *Attorney, Agent, or Firm* — Barnes & Thornburg LLP

(57)          ABSTRACT

A femur-first orthopaedic surgical procedure may include using a surgical navigation system to perform one or more initial measurements on a femur of a patient, a tibia of the patient, or both and to develop a surgical plan for the orthopaedic surgical procedure based on the one or more initial measurements, performing a first resection of the femur, using the surgical navigation system to perform one or more later measurements of the tibia that were inaccessible prior to the first resection of the femur and to confirm the surgical plan based on the one or more later measurements of the tibia, performing a tibial resection of the tibia based on a planned tibial resection plane of the surgical plan after confirming the surgical plan, and performing additional resections of the femur based on planned femoral resection planes of the surgical plan after confirming the surgical plan.

20 Claims, 11 Drawing Sheets

(56)          References Cited

OTHER PUBLICATIONS

Depuy Synthes, "Attune Knee System, Intuition Instruments, Sur-
gical Technique," 2022, 136 pages.
Chowhipknee, "Conformis iUni—Unicompartmental Knee Implant,"
available at https://www.youtube.com/watch? V=ZylGnLbrHbw,
Aug. 10, 2010.

* cited by examiner

SYSTEM AND METHODS FOR FEMUR-FIRST ORTHOPAEDIC SURGICAL PROCEDURES

TECHNICAL FIELD

The present disclosure relates generally to orthopaedic surgical procedures and, more particularly, to systems and methods for femur-first orthopaedic surgical procedures.

BACKGROUND

Joint arthroplasty is a well-known surgical procedure by which a diseased and/or damaged natural joint is replaced by a prosthetic joint, which may include one or more orthopaedic implants. To facilitate the replacement of the natural joint with the prosthetic joint, orthopaedic surgeons may use a variety of orthopaedic surgical instruments such as, for example, surgical saws, cutting guides, reamers, broaches, drill guides, drills, positioners, insertion tools and/or other surgical instruments. A surgeon may use manual instruments such as cutting blocks or other cutting guides to perform the various resections in an orthopaedic procedure. Alternatively, or in addition, a surgeon may use a computer-assisted surgical navigation system, such as a robotic-assisted surgical system, to perform the various resections in an orthopaedic procedure.

A robotic-assisted surgical system may be used to perform a total knee arthroplasty (TKA) or unicompartmental knee arthroplasty (UKA) surgical procedure. Typical robotic-assisted surgical systems may use a segmented bone model generated from pre-operative medical imaging. Certain image-free systems, as well as conventional manual techniques for UKA, require resection of the tibia prior to resection of the femur.

SUMMARY

According to one aspect, a method for an orthopaedic surgical procedure may comprise performing, using a surgical navigation system, one or more initial measurements on a femur of a patient, a tibia of the patient, or both; developing, using the surgical navigation system, a surgical plan for the orthopaedic surgical procedure based on the one or more initial measurements; performing a first resection of the femur; performing, using the surgical navigation system, one or more later measurements of the tibia that were inaccessible prior to the first resection of the femur; confirming, using the surgical navigation system, the surgical plan based on the one or more later measurements of the tibia; performing a tibial resection of the tibia based on a planned tibial resection plane of the surgical plan after confirming the surgical plan; and performing additional resections of the femur based on planned femoral resection planes of the surgical plan after confirming the surgical plan.

In some embodiments, the first resection may be a posterior femoral resection. In other embodiments, the first resection may be a distal femoral resection.

In some embodiments, performing the one or more later measurements of the tibia may comprise recording one or more posterior points of a compartment of the tibia. Recording the one or more posterior points may comprise recording a most-posterior point of the compartment of the tibia. Performing the one or more later measurements of the tibia may comprise recording a most-lateral or most-medial point of a compartment of the tibia.

In some embodiments, performing the one or more later measurements of the tibia may comprise recording a natural slope of the tibia. Recording the natural slope of the tibia may comprise sensing a navigated pointer instrument of the surgical navigation system while an elongated body of the navigated pointer instrument is aligned with the natural slope of the tibia.

In some embodiments, performing the one or more later measurements of the tibia may comprise sensing a navigated pointer instrument of the surgical navigation system while a tip of the navigated pointer instrument contacts a point on the tibia that was inaccessible to the navigated pointer instrument prior to the first resection of the femur.

In some embodiments, performing the one or more later measurements of the tibia may comprise scanning a surface of the tibia with a laser scanner, a white light scanner, or a structured light scanner.

In some embodiments, performing the first resection of the femur may comprise resecting the femur along a planned posterior femoral resection plane or a planned distal femoral resection plane of the surgical plan. In other embodiments, performing the first resection of the femur may comprise resecting the femur along a preliminary plane that is either (i) posterior of a planned posterior femoral resection plane of the surgical plan or (ii) distal of a planned distal femoral resection plane of the surgical plan. In such embodiments, performing the additional resections of the femur based on planned femoral resection planes of the surgical plan after confirming the surgical plan may comprise resecting the femur along the planned posterior femoral resection plane of the surgical plan and resecting the femur along the planned distal femoral resection plane of the surgical plan.

In some embodiments, confirming the surgical plan based on the one or more later measurements of the tibia may comprise modifying the surgical plan based on the one or more later measurements of the tibia. In embodiments where the surgical plan developed prior to performing the one or more later measurements of the tibia includes the planned tibial resection plane, modifying the surgical plan based on the one or more later measurements of the tibia may comprise modifying the planned tibial resection plane. In embodiments where the surgical plan developed prior to performing the one or more later measurements of the tibia does not include the planned tibial resection plane, modifying the surgical plan based on the one or more later measurements of the tibia may comprise adding the planned tibial resection plane to the surgical plan.

In some embodiments, modifying the surgical plan based on the one or more later measurements of the tibia may comprise setting the planned tibial resection plane to mimic a natural slope of the tibia. Modifying the surgical plan may further comprise setting the planned femoral resection planes to mimic a natural joint space in flexion and to achieve a balanced joint space in extension.

In some embodiments, performing a tibial resection after confirming the surgical plan may comprise performing a horizontal tibial resection of the tibia based on a planned horizontal tibial resection plane of the surgical plan and performing a vertical tibial resection of the tibia based on a planned vertical tibial resection plane of the surgical plan.

In some embodiments, performing the first resection of the femur, performing the tibial resection of the tibia, and performing the additional resections of the femur may each comprise operating a robotic assisted surgery device in communication with the surgical navigation system, wherein movement of the robotic assisted surgery device is constrained according to surgical plan.

According to another aspect, a method for an orthopaedic surgical procedure may comprise performing, using a surgical navigation system, one or more femoral measurements on a femur of a patient; developing, using the surgical navigation system, a surgical plan for the orthopaedic surgical procedure based on the one or more femoral measurements; performing at least one resection of the femur based on the surgical plan; performing, using the surgical navigation system after performing the at least one resection of the femur, one or more tibial measurements of one or more posterior points on a tibia of the patient; confirming, using the surgical navigation system, the surgical plan based on the one or more tibial measurements; and performing a tibial resection of the tibia based on the surgical plan after confirming the surgical plan.

In some embodiments, confirming the surgical plan based on the one or more tibial measurements may comprise modifying the surgical plan based on the one or more tibial measurements.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
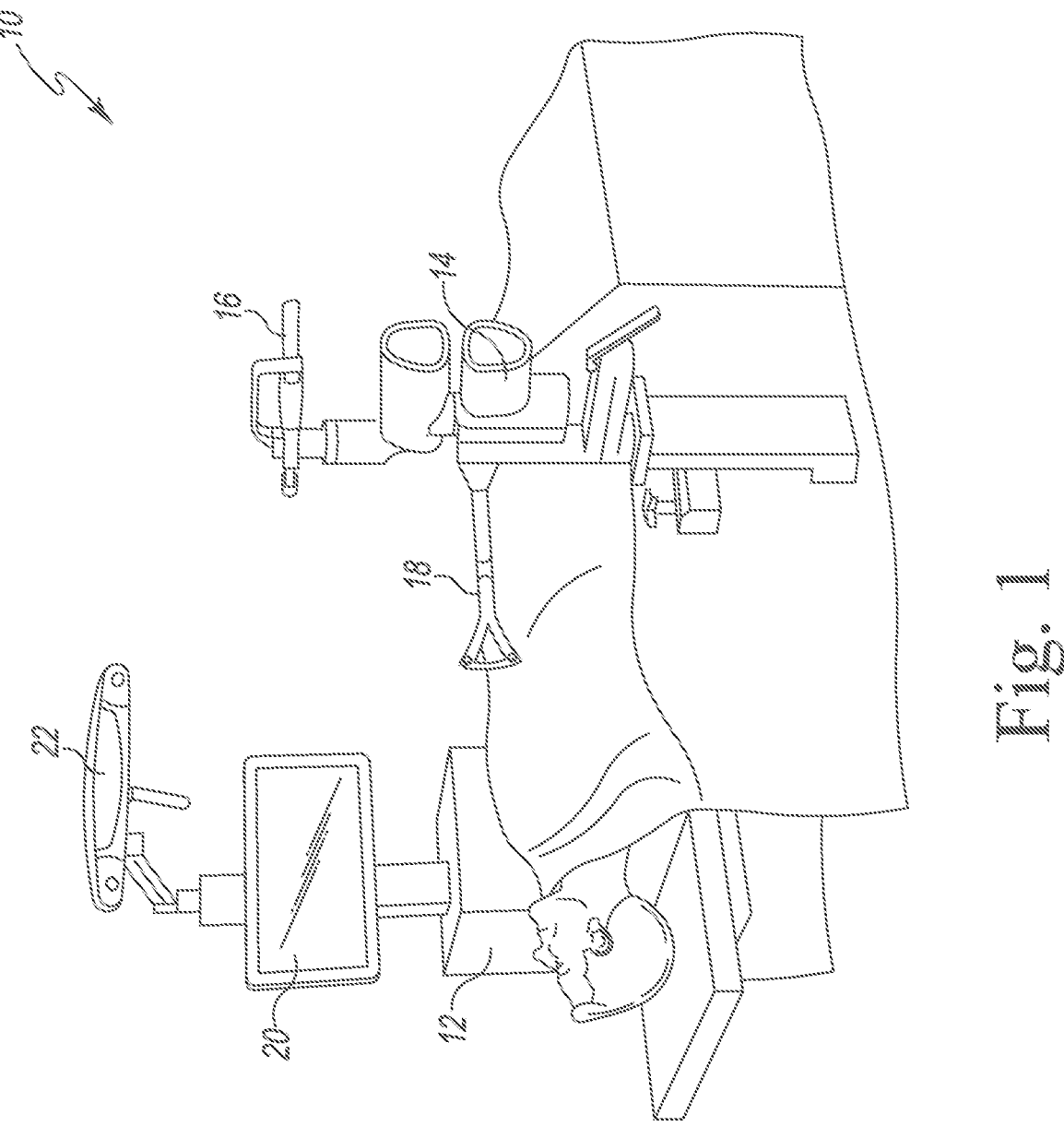
FIG. 1 is a schematic diagram of a system for planning and assisting an orthopaedic surgical procedure.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a surgical system 10 is used during an orthopaedic surgical procedure, such as a unicompartmental knee arthroplasty (UKA) or a total knee arthroplasty (TKA) procedure. During that procedure, an orthopaedic surgeon uses the system 10 to perform a first resection of the patient's femur (e.g., a posterior femoral resection or a distal femoral resection). After performing this first resection, the surgeon uses the system 10 to register or otherwise measure part or all of the patient's tibial surface that is now accessible. The surgeon then uses the system 10 to confirm a surgical plan (including modifying the surgical plan, as needed or desired) based on the tibial measurements performed after the first femoral resection. (As used in the present disclosure, "based on" does not exclude the presence of additional inputs, e.g., the surgeon may use additional information, beyond the tibial measurements performed after the first femoral resection, when confirming the surgical plan.) The surgeon uses the confirmed surgical plan with the system 10 to complete the orthopaedic surgical procedure.

Thus, the system 10 may allow the surgeon to accurately resurface the patient's anatomy, which may achieve (or mimic) a natural joint space in flexion and a balanced joint space in extension. By performing the first femoral resection (e.g., a posterior femoral resection or a distal femoral resection) before registering the natural tibial surface, the system 10 may provide improved resurfacing accuracy compared to manual techniques that perform tibial resection first. Further, the system 10 may provide accurate resurfacing without requiring preoperative imaging, and thus may advantageously be used when preoperative imaging is not available (e.g., in trauma situations). Of course, the system 10 may also be used with preoperative imaging, in which case registration of the patient's natural tibia may be used to confirm a surgical plan generated with preoperative imaging (including modifying the surgical plan). Additionally, performing at least one resection of the femur prior to tibial resection may allow for easier removal of the meniscus and/or other soft tissue around the tibia by the surgeon, which may reduce the time required to complete the orthopaedic surgical procedure. Performing at least one resection of the femur first may also allow for easier removal of the bone chip(s) resulting from tibial resection, which may further reduce surgical time.

As shown in FIG. 1, the system 10 includes a surgical planning and assistance device 12, a robotic surgical device 14, and multiple registration tools 18. The surgical planning and assistance device 12 may be embodied as any type of computer system capable of performing the functions described herein. For example, the surgical planning and assistance device 12 may be embodied as, without limitation, a workstation, a desktop computer, a laptop computer, a special-purpose compute device, a server, a rack-mounted server, a blade server, a network appliance, a web appliance, a tablet computer, a smartphone, a consumer electronic device, a distributed computing system, a multiprocessor system, and/or any other computing device capable of performing the functions described herein. Accordingly, the illustrative surgical planning and assistance device 12 may include components commonly found in a computer such as a processor, an I/O subsystem, memory, a data storage device, a communication subsystem, and various input/output devices. Additionally, although the surgical planning and assistance device 12 is illustrated in FIG. 1 as embodied as a single computer, it should be appreciated that the surgical planning and assistance device 12 may be embodied as multiple devices cooperating together to facilitate the functionality described below. For example, in some embodiments, the system 10 may include a base station and a satellite station or other combination of computing devices. Additionally or alternatively, in some embodiments, the surgical planning and assistance device 12 may be embodied as a "virtual server" formed from multiple computer systems distributed across a network and operating in a public or private cloud.

As shown in FIG. 1, the surgical planning and assistance device 12 includes a display 20. The display 20 may be embodied as any type of display capable of displaying digital images or other information, such as a liquid crystal display (LCD), a light emitting diode (LED), a plasma display, a cathode ray tube (CRT), or other type of display device. In some embodiments, the display 20 may be coupled to a touch screen to allow user interaction with the surgical planning and assistance device 12. Other user inputs, such as foot pedals, may also be used.

The surgical planning and assistance device 12 further includes one or more cameras 22. Each of the cameras 22 may be embodied as a digital camera or other digital imaging device coupled to the surgical planning and assistance device 12. Each camera 22 includes an electronic image sensor, such as an active-pixel sensor (APS), e.g., a complementary metal-oxide-semiconductor (CMOS) sensor, or a charge-coupled device (CCD). In the illustrative embodiment, multiple cameras 22 are arranged in an array and are thus capable of determining distance to objects imaged by the cameras 22.

The robotic surgical device 14 may be embodied as any type of robot capable of performing the functions described herein. Illustratively, the robotic surgical device 14 is embodied as a robotic arm that may be attached to a surgical table or otherwise positioned near a patient during the orthopaedic surgical procedure. The robotic surgical device 14 includes a surgical tool 16, illustratively embodied as a surgical saw 16. In use, the robotic surgical device 14 supports the surgical saw 16 and may constrain movement of the surgical saw 16 within a resection plane specified in a surgical plan. The surgeon may activate the surgical saw 16 and perform the resection with the surgical saw 16 while the robotic surgical device 14 constrains movement of the surgical saw 16 to the resection plane. Although illustrated with a surgical saw 16, it should be understood that, in other embodiments, the robotic surgical device 14 may include, or be used with, one or more other surgical instruments, such as, for example, surgical burrs, chisels, impactors, reamers, and other powered surgical tools. The robotic surgical device 14 may illustratively be embodied as a VELYS™ Robotic-Assisted Solution, commercially available from DePuy Synthes Products, Inc. of Warsaw, Indiana.

The surgical planning and assistance device 12 and the robotic surgical device 14 may be configured to transmit and receive data with each other and/or other devices of the system 10 over a network. The network may be embodied as any number of various wired and/or wireless networks. For example, the network may be embodied as, or otherwise include, a wired or wireless local area network (LAN), a wired or wireless wide area network (WAN), a cellular network, and/or a publicly-accessible, global network such as the Internet. As such, the network include any number of additional devices, such as additional computers, routers, stations, and switches, to facilitate communications among the devices of the system 10.

The system 10 further includes a number of registration tools 18. As described further below, in use, the surgical planning and assistance device 12 may track the location of the registration tools 18 in space using the array of cameras 22. For example, each registration tool 18 may include a number of hydrophobic optical reflectors arranged in a predetermined pattern visible to the cameras 22. Illustratively, the registration tools 18 include markers secured to the robotic device 14 and to the associated surgical tool 16, which allow the device 12 to track the location of the robotic device 14 and/or the surgical tool 16. As described further below, the system 10 may also track multiple arrays configured to each be secured to one of the patient's bones and a pointer that may be temporarily positioned by a surgeon relative to anatomical landmarks of the patient while the pointer is observed by the cameras 22. As such, the registration tools 18 may be used for registration and tracking of the patient's bony anatomy during the orthopaedic surgical procedure. Although illustrated as including registration tools 18 suitable for optical tracking with the cameras 22, it should be understood that in some embodiments, the system 10 may use electromagnetic tracking or other position tracking technology for tracking the registration tools 18.

Figure 2:
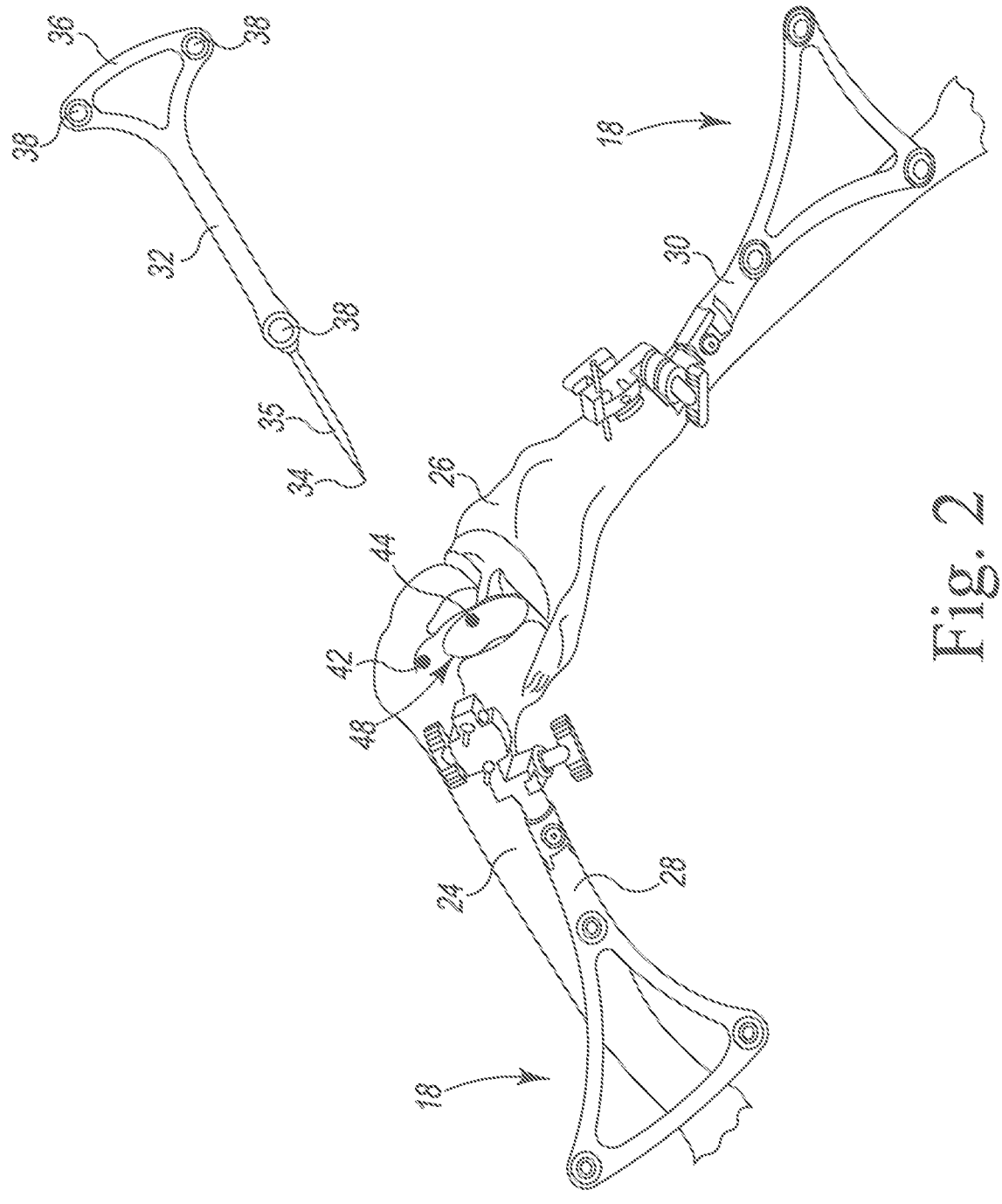
FIGS. 2 and 3 are perspective diagrams of a femur and a tibia of a patient with surgical instruments during performance of the orthopaedic surgical procedure.
Figure 3:
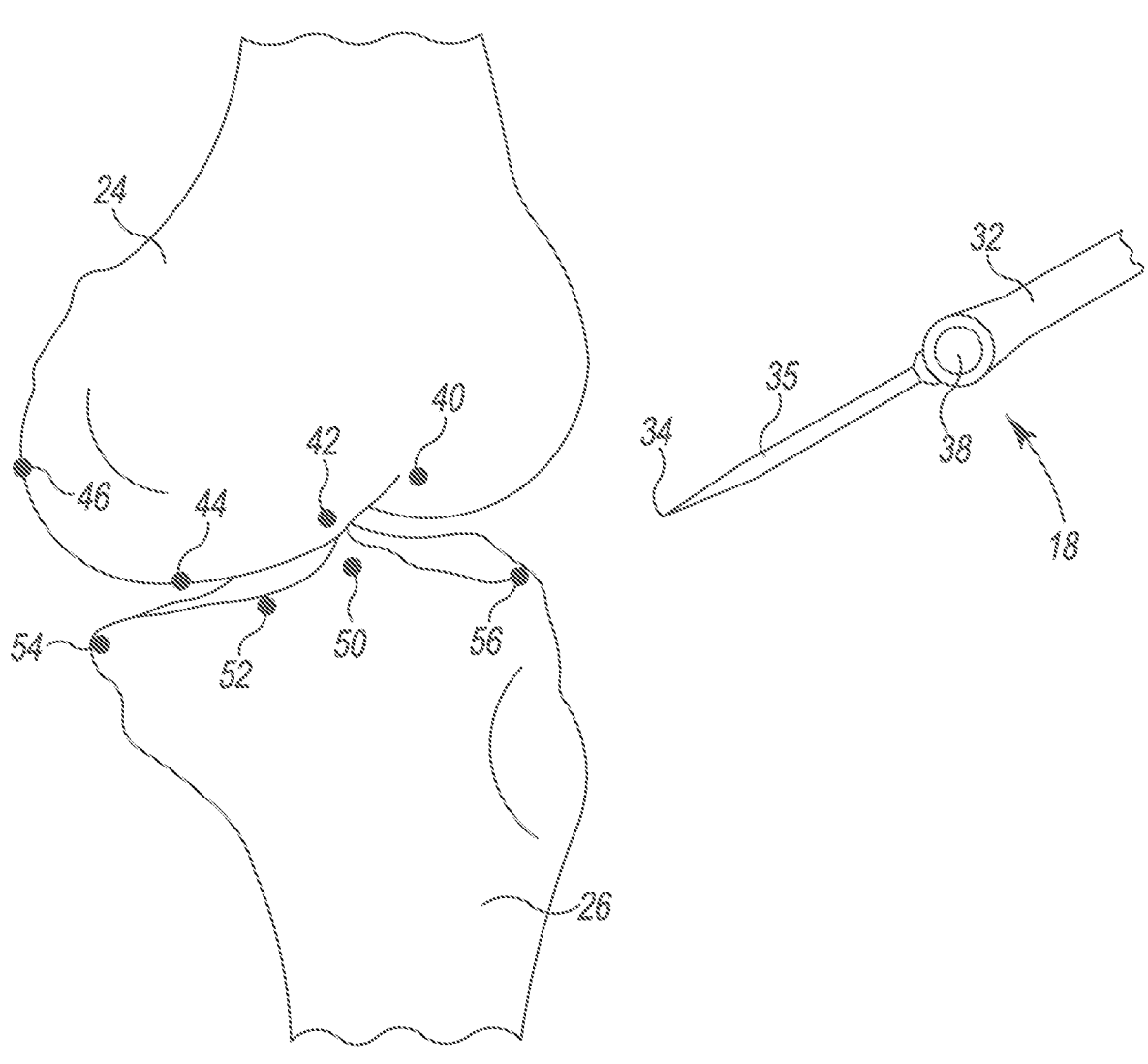

Referring now to FIGS. 2 and 3, a surgeon may perform initial registration with the system 10 during a unicompartmental knee arthroplasty (UKA) surgical procedure. Although illustrated herein in connection with a UKA surgical procedure, it should be understood that the system 10 may be used with other orthopaedic surgical procedures, such as total knee arthroplasty (TKA) surgical procedures. To perform registration, the surgeon attaches arrays 28, 30 (which are registration tools 18) to the patient's femur 24 and tibia 26, respectively. The device 12 uses the cameras 22 to track the position of the bone arrays 28, 30 and thus register relative positions of the patient's femur 24 and tibia 26. The surgeon may manipulate the patient's femur 24 and tibia 26 in order to capture registration data for various kinematic axes and over a range of motion. For example, the surgeon may rotate the femur 24 to acquire hip center. As another example, the surgeon may acquire relative positions of the femur 24 and the tibia 26 over a range of motion from full extension to maximum flexion. Using this data, combined with data relating to the shape of the femur 24 and the shape of the tibia 26 (such as the points and/or surfaces discussed below, or shape information derived therefrom), the system 10 may determine any number of flexion and extension gaps between the femur 24 and the tibia 26 as part of the initial registration.

The surgeon also uses a pointer 32 to acquire various points on the patient's bony anatomy during the initial registration. The pointer 32 is a registration tool 18 that may be used with the system 10 for surgical navigation and/or robotic assisted surgery. The illustrative pointer 32 includes an elongated body 35 that extends from a tip 34 to a triangular frame 36. The frame 36 supports hydrophobic optical reflectors 38, which may be tracked by the device 12 using the cameras 22 as described above. In use, the surgeon positions the tip 34 (or elongated body 35) of the pointer 32 in a desired location. The device 12, using the camera 22, tracks the location of the reflectors 156 and, based on those tracked locations, determines the corresponding position of the tip 34 (or elongated body 35).

Illustratively, the surgeon may use the pointer 32 to register positions on the patient's anatomy that are accessible prior to performing bone resections or other bone cuts. For example, the surgeon may create a tibial checkpoint and then acquire the position of the tibial checkpoint with the pointer 32, the surgeon may create a femur checkpoint and acquire the position of the femur checkpoint with the pointer 32, and the surgeon may acquire the positions of the medial malleolus and the lateral malleolus with the pointer 32. As best seen in FIG. 3, the surgeon may use the pointer 32 to acquire a femur center. As shown in FIGS. 2 and 3, the surgeon may use the pointer 32 to acquire a femoral knee center 40, a femoral anterior point 42, a femoral distal point 44, and a femoral posterior point 46. As best seen in FIG. 2, the surgeon may use the pointer 32 to acquire a femoral condyle surface 48. To capture the femoral condyle surface 48, the surgeon may move the tip 34 of the pointer 32 across the surface 48, and the system 10 may capture multiple positions on the surface 48. Those captured positions may be represented as a point cloud or other collection of location data associated with the femoral condyle surface 48.

The surgeon may also capture accessible locations on the patient's tibia 26. As best shown in FIG. 3, the surgeon may use the pointer 32 to acquire a tibia knee center 50, a tibial anterior point 52, and in some embodiments a tibial most-medial point 54 and/or a tibial most-lateral point 56. In some embodiments, the surgeon may register these points on the tibia 26 after performing a first resection of the femur, as described below. It will be appreciated that, in other embodiments, the surgeon may capture a different number and/or arrangement of bony anatomy landmarks or other features.

Figure 4:
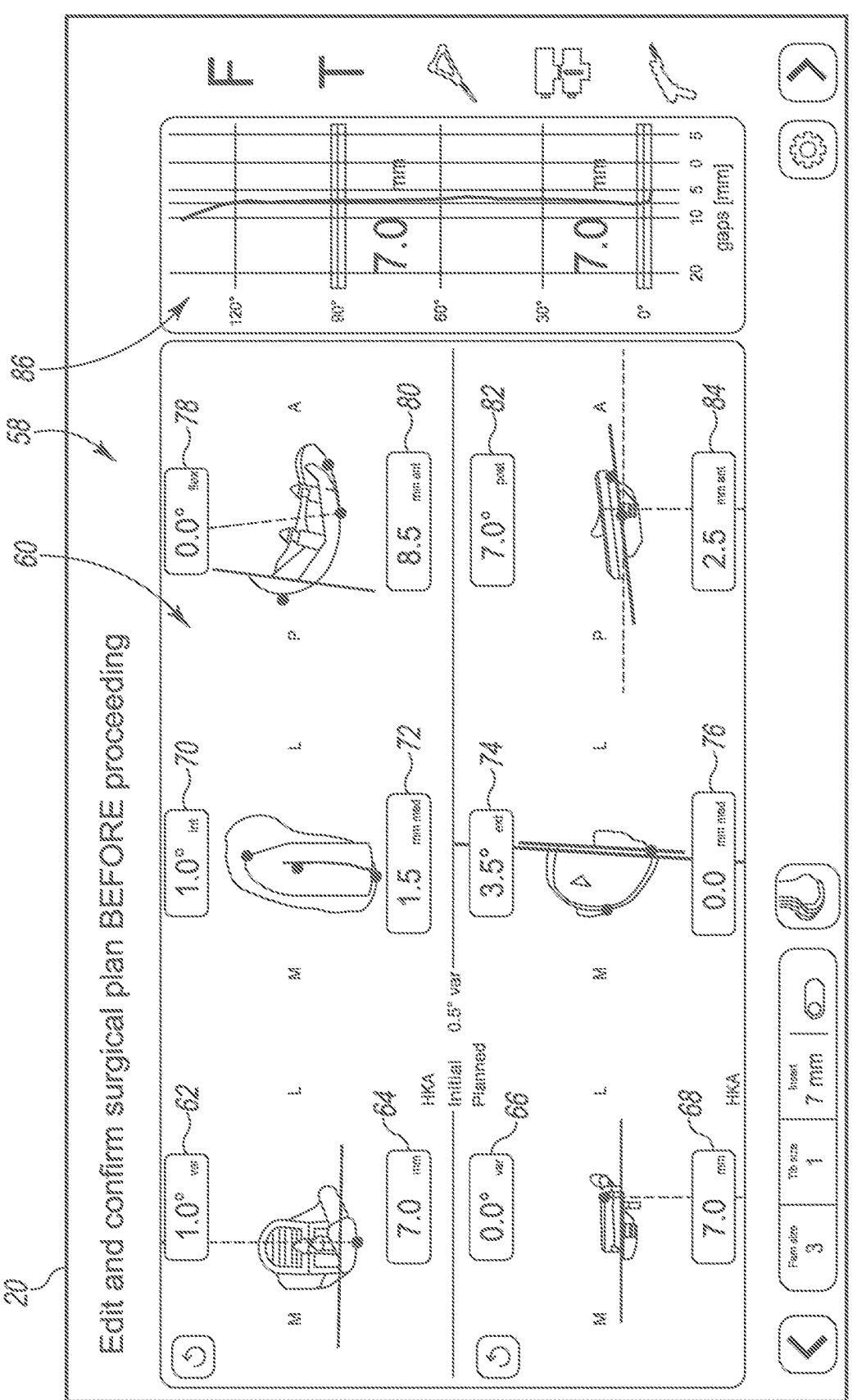
FIG. 4 is a schematic diagram illustrating a display interface of the system of FIG. 1 during performance of the orthopaedic surgical procedure.

Referring now to FIG. 4, the surgeon may use the device 12 to develop a surgical plan based on the initial registration. As used herein, "developing a surgical plan" (and similar phrases) may refer to creating new surgical plan and/or modifying an already existing surgical plan. As shown, the display 20 of the device 12 is configured to display an illustrative user interface 58. The user interface 58 includes an interactive representation 60 of a surgical plan. The surgical plan includes one or more surgical parameters, such as the heights and angles of various planned resection planes, which may be used to control the robotic surgical device 14. The surgical plan may be based on predetermined surgeon preferences or otherwise based on one or more default values. Additionally or alternatively, in some embodiments, part or all of the surgical plan may be determined preoperatively, for example using one or more preoperative medical images. As shown, the interactive representation 60 includes graphical representations of the patient's anatomy associated prosthetic components. The interactive representation 60 also includes textual and/or numerical representations of various surgical parameters. Those surgical parameters may be interactively viewed and/or edited by the surgeon or other user before continuing with the surgical procedure.

Illustratively, the interactive representation 60 includes user interface elements for viewing and/or editing a femoral prosthesis *varus/valgus* angle 62, a posterior femoral resection height 64, a tibial prosthesis *varus/valgus* angle 66, a tibial resection height 68, a femoral prosthesis internal/external rotation angle 70, a femoral prosthesis medial/lateral shift 72, a tibial prosthesis internal/external rotation angle 74, a tibial prosthesis medial/lateral shift 76, a femoral prosthesis flexion/extension angle 78, a femoral prosthesis anterior/posterior shift 80, a tibial slope angle 82, and a tibial prosthesis anterior/posterior shift 84. The interactive representation 60 may further include additional user interface elements for other information or surgical parameters, including hip-knee-ankle (HKA) or mechanical alignment, implant size, insert size, or other information.

As shown, the user interface 58 further includes a joint balance graph 86, which is an interactive representation of joint gaps through a range of motion (e.g., through extension and flexion). Illustratively the joint balance graph 86 includes a graphical representation of distance between articulating surfaces of the femur 24 and the tibia 26 based on captured registration information for the relative positions of the femur 24 and the tibia 26, captured registration information for features on the surfaces of the femur 24 and the tibia 26, and current values of various surgical parameters of the surgical plan. The joint balance graph 86 may be updated based on changes to the surgical plan. For example, adjusting the tibial resection height 68 may change the values shown in the joint balance graph 86. The surgeon may use the user interface 58 to perform an initial leg alignment and balance.

Figure 5:
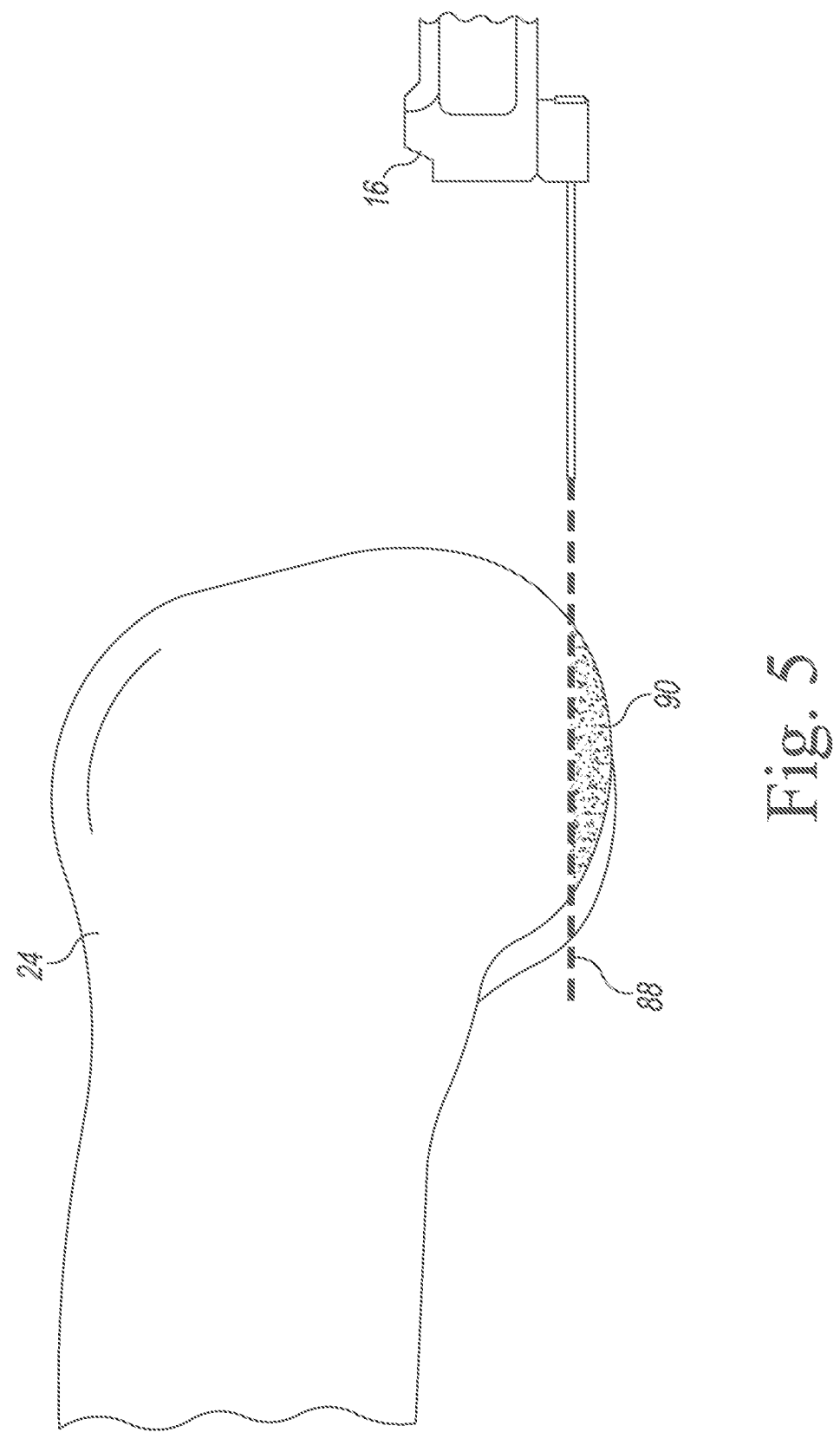
FIG. 5 is a perspective diagram illustrating a posterior femoral resection performed during the orthopaedic surgical procedure.

Referring now to FIG. 5, in the illustrative embodiment, the surgeon uses the robotic surgery device 14 to perform a posterior femoral resection. The surgeon may place the tip 34 of the pointer 32 on the previously marked checkpoint on the femur 24 to verify that the femur array 28 has not moved. The device 12 may display a representation of the relative locations of the tip 34 and the femur checkpoint, and may indicate whether the tip 34 is positioned on the predetermined position of the femur checkpoint. For example, the display 22 may include a graphical representation of the relative locations of the tip 34 and the femur 24 and a numerical representation of the distance between the current location of the tip 34 and the femur checkpoint.

Once the surgeon verifies the location of the femur checkpoint, the robotic surgery device 14 positions the surgical saw 16 in a posterior femoral resection plane 88. The posterior femoral resection plane 88 is defined by the surgical plan described above, and may be measured relative to a posterior condyle surface 90. For example, the posterior femoral resection plane 88 may be positioned at a certain distance in millimeters from the most-posterior point of the posterior condyle 90 extracted from the posterior condyle acquisition, i.e., the posterior femoral resection height 64. In some embodiments, the resection plane 88 may be positioned some distance short of the posterior femoral resection height 64 defined in the surgical plan. In those embodiments, the final posterior femoral resection height 64 of the surgical plan may be further adjusted before making a final cut on the posterior femur. The robotic surgical system 14 supports the surgical saw 16 and may constrain movement of the surgical saw 16 within the posterior femoral resection plane 88 while the surgeon uses the surgical saw 16 to perform the posterior femoral resection.

Figure 6:
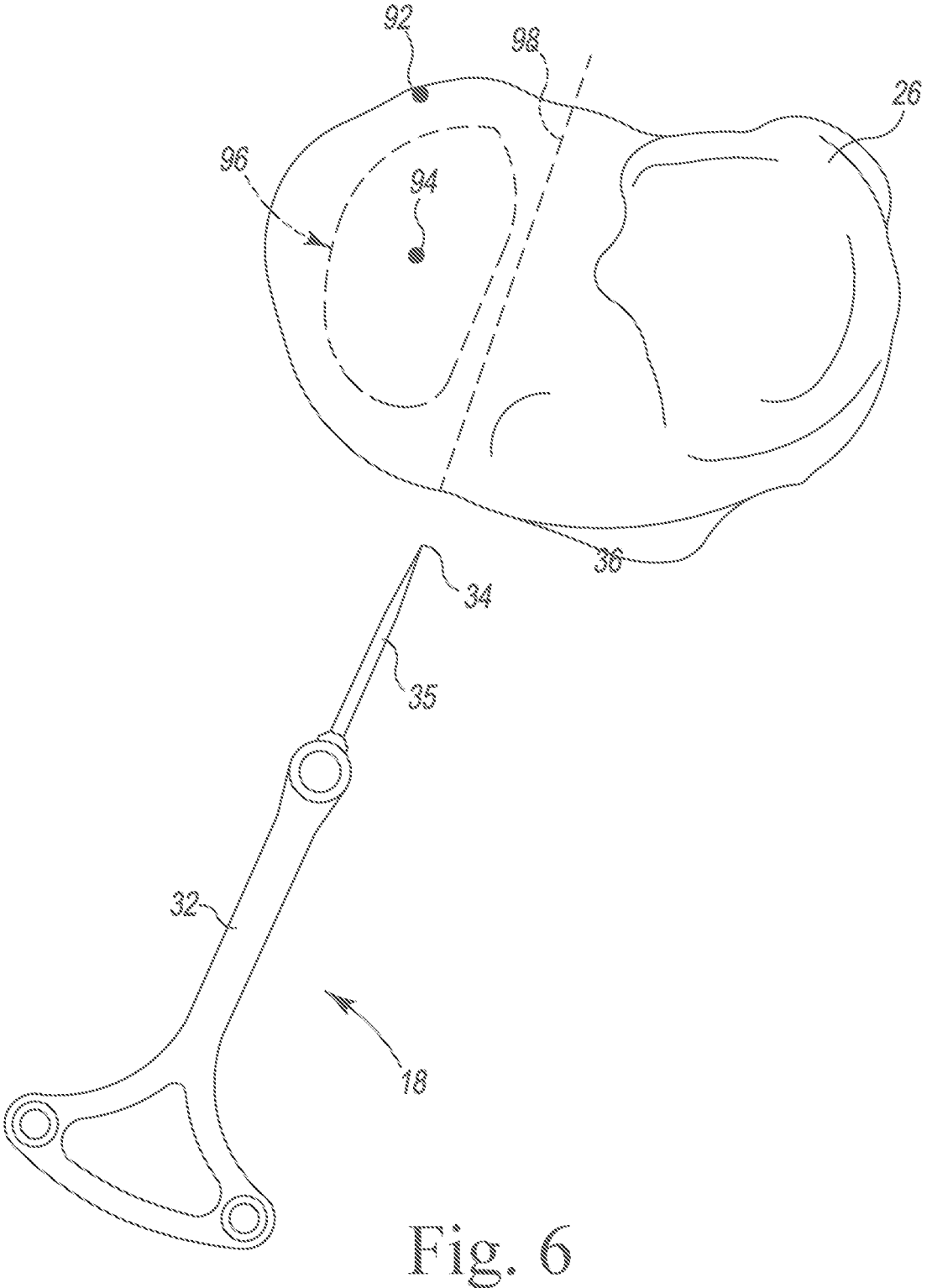
FIG. 6 is a perspective diagram illustrating registration of a tibial surface performed during the orthopaedic surgical procedure.

Referring now to FIG. 6, after performing the posterior femoral resection in the illustrative embodiment, the surgeon uses the pointer 32 to register or otherwise measure features of the patient's natural tibia 26. The surgeon may position the tip 34 of the pointer 32 on one or more locations of the patient's tibia 26 that were previously inaccessible due to tightness of the knee, i.e., the tibia 26 and the femur 24 being in close contact throughout their entire range of motion, but that are currently accessible after performing the first femoral resection. In some embodiments, the surgeon may also remove some or all of the meniscus (and/or other soft tissue) after the first femoral resection and prior to measuring the tibia 26. In other embodiments, the tip 34 of the pointer 32 may be positioned on the meniscus, and the device 12 may account for the presence of the meniscus during measurement of the tibia 26.

The surgeon may use the pointer 32 to acquire a tibial most-posterior point 92 and a tibial resection reference point 94. The surgeon may use the pointer 32 to capture a tibial plateau surface 96. Similar to the femoral condyle surface 48 described above, the surgeon may move the tip 34 of the pointer 32 across the surface 96, and the system 10 may capture multiple positions on the surface 96. Those captured positions may be represented as a point cloud or other collection of location data associated with the tibial plateau surface 96. Additionally or alternatively, in some embodiments, the surgeon may use the pointer 32 to acquire other locations on the tibia 26 (e.g., a most-medial point 54 and/or a most-lateral point 56 on the tibia 26) after the first femoral resection.

The surgeon may also use the pointer 32 to capture a natural slope 98 of the tibia 26. To capture the natural slope 98, the surgeon may align the elongated body 35 of the pointer 32 with the tibial plateau surface 96. The system 10 captures the position and orientation of the elongated body 35 of the pointer 32 and, based on that position and orientation, determines the relative angle of the natural slope 98. In some embodiments, the surgeon may also capture a vertical cut line for a unicompartmental tibial implant, which may be the location for the vertical cut nearest the tibial midline.

Although illustrated as capturing tibial registration and other measurements using the pointer 32, it should be understood that in some embodiments, the system 10 may capture tibial measurements using a laser scanner, a white light scanner, a structured light scanner, or other surface scanner. As another example, the system 10 may capture tibial measurements using an ultrasound imaging scanner or other volumetric scanner.

Figure 7:
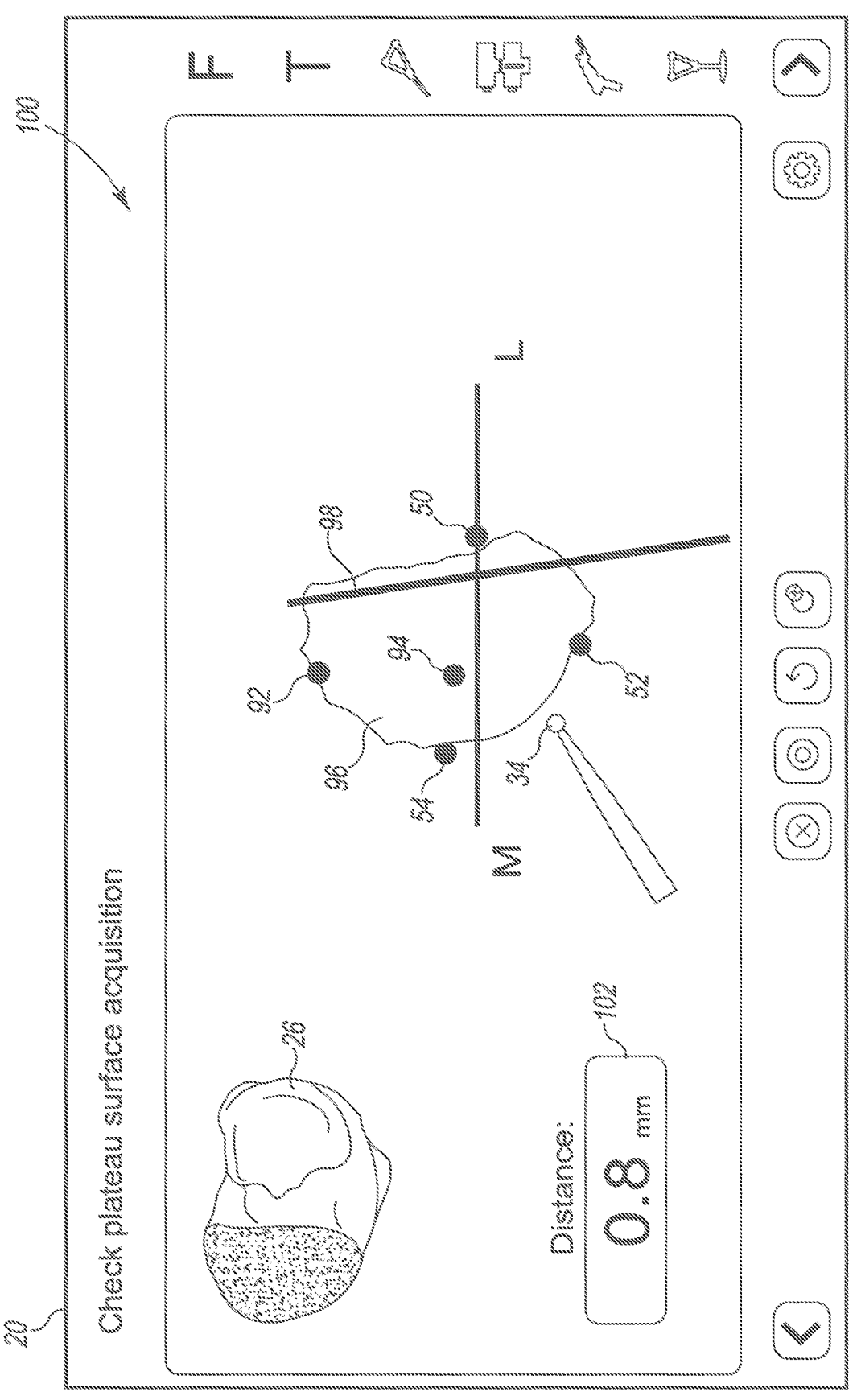
FIG. 7 is a schematic diagram illustrating another display interface of the system of FIG. 1 during performance of the orthopaedic surgical procedure.

Referring now to FIG. 7, after acquiring tibial registration or other measurements, the surgeon may confirm the registration using the device 12. As shown, the display 20 of the device 12 is configured to display an illustrative user interface 100 that may be used to verify tibial registration. The surgeon positions the tip 34 (or elongated body 35) of the pointer 32 on various parts of the patient's tibia 26, the device 12 determines the position of the pointer 32, and the device 12 compares the current position of the pointer 32 to one or more acquired features of the tibia 26. The user interface 100 displays one or more representations of the relative positions of the pointer 32 and the acquired features of the tibia 26, including a graphical representation and a numeric distance display 102. In the illustrative embodiment shown in FIG. 7, the user interface 100 displays the distance 102 between the tip 34 of the pointer 32 and the acquired tibial plateau surface 96. Accordingly, the surgeon may verify that when the tip 34 is positioned on the surface of the tibial plateau 96, the distance 102 displays zero (or an acceptably small distance). Similarly, the surgeon may verify other captured landmarks or other features of the patient's tibia 26, including the tibial most-posterior point 92, the tibial resection reference point 94, the tibial most-medial point 54, the tibial knee center 50, and/or the natural slope 98 of the tibia 26.

Referring again to FIG. 4, after verifying acquisition of the tibial registration or other tibial measurements, the surgeon may use the device 12 to confirm the surgical plan based on the tibial registration. As used herein, "confirming a surgical plan" (and similar phrases) may refer to approving the surgical plan with or without modification; in other words, confirming the surgical plan may optionally include modifying the surgical plan. As described above, the display 20 is configured to display the illustrative user interface 58 for viewing and confirming the surgical plan, as well as the joint balance graph 86. In particular, the joint balance graph 86 may be updated based on the acquired tibial registration. The surgeon may also modify one or more parameters of the surgical plan based on the acquired tibial registration. In particular, the surgeon may modify the planned tibial resection plane (e.g., the tibial slope angle 74) of the surgical plan to mimic the natural slope 98 of the tibia 26. The surgeon may also modify one or more parameters of the surgical plan (e.g., the planned femoral resection planes) to mimic a natural joint space when the femur 24 and tibia 26 are in flexion and to achieve a balanced joint space when the femur 24 and tibia 26 are in extension. The surgeon confirms the surgical plan when the surgical parameters of the surgical plan and the joint balance graph 86 are satisfactory.

Figure 8:
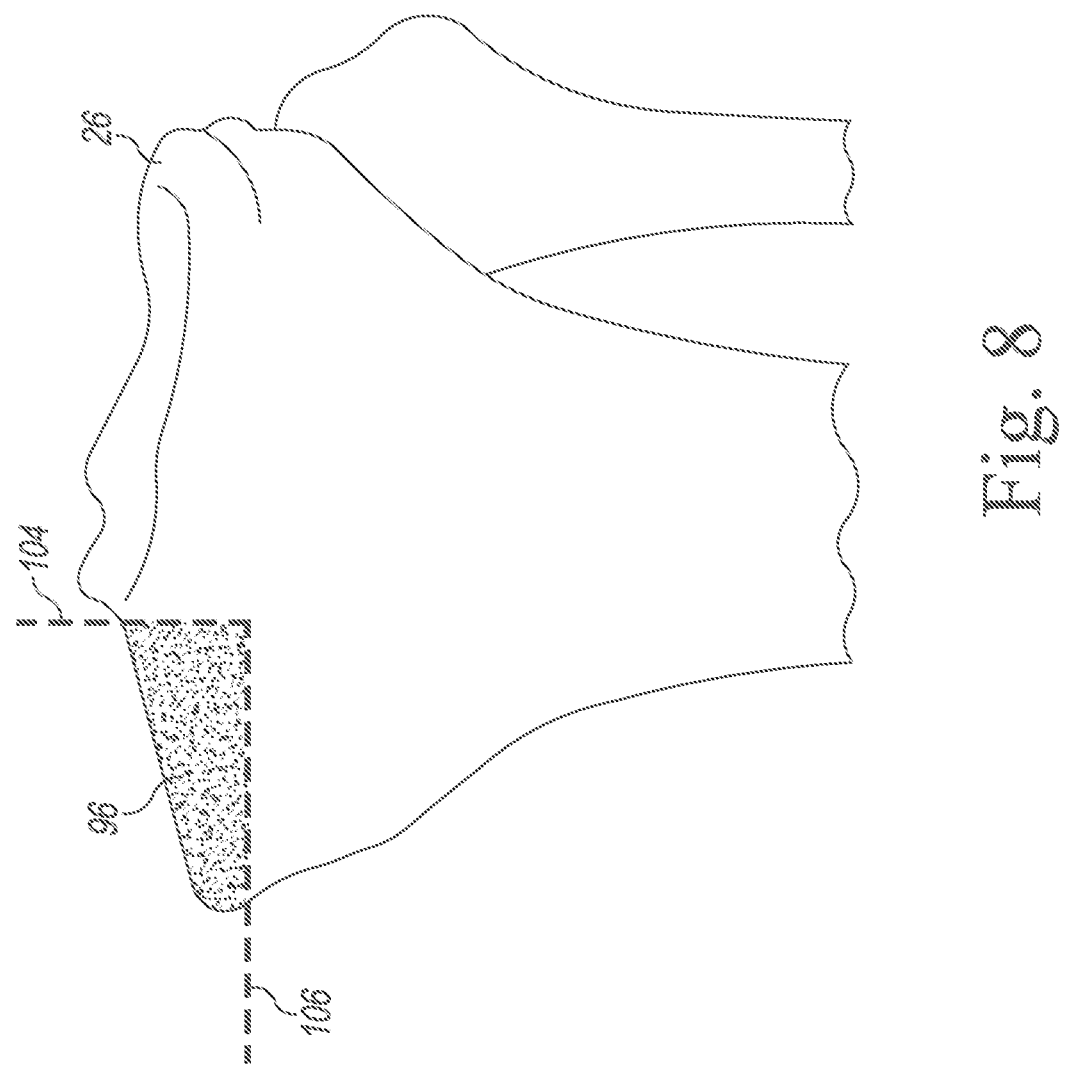
FIG. 8 is a perspective diagram illustrating tibial resections performed during the orthopaedic surgical procedure.

Referring now to FIG. 8, after confirming the surgical plan, the surgeon performs one or more tibial resections. The surgeon may place the tip 34 of the pointer 32 on the previously marked checkpoint on the tibia 26 to verify that the tibia array 30 has not moved. The device 12 may display a representation of the relative locations of the tip 34 and the tibia checkpoint, and may indicate whether the tip 34 is positioned on the predetermined position of the tibia check- point. For example, the display 22 may include a graphical representation of the relative locations of the tip 34 and the tibia 26 and a numerical representation of the distance between the current location of the tip 34 and the tibia checkpoint.

Once the surgeon verifies the location of the tibia check- point, the surgeon uses the robotic surgery device 14 to perform a horizontal tibial resection. The robotic surgery device 14 positions the surgical saw 16 in a horizontal tibial resection plane 106. The horizontal tibial resection plane 106 is defined by the surgical plan described above, and may be measured relative to the tibial resection reference point 94 and/or the tibial plateau surface 96. For example, the horizontal tibial resection plane 106 may be positioned at a certain distance in millimeters from the tibial resection reference point 94, i.e., the tibial resection height 68. The horizontal tibial resection plane 106 may be positioned at an angle defined by the tibial slope angle 74. The robotic surgical system 14 supports the surgical saw 16 and may constrain movement of the surgical saw 16 within the horizontal tibial resection plane 106 while the surgeon uses the surgical saw 16 to perform the horizontal tibial resection.

Additionally, either before or after the horizontal tibial resection, the surgeon uses a reciprocating saw to perform the vertical tibial resection. In the illustrative embodiment, the surgeon couples a reciprocating saw handpiece (not shown) to the robotic surgical device 14 and then manually positions the reciprocating saw blade in a vertical tibial resection plane 104. The vertical tibial resection plane 104 is defined by the surgical plan described above. For example, the vertical tibial resection plane 104 may be positioned at a certain distance from a landmark of the tibia 26, and may be angled at a certain rotation angle, such as the tibial prosthesis rotation angle 82. After manually positioning the reciprocating saw blade, the robotic surgical device 14 moves down and allows the surgeon to perform the vertical tibial resection if the reciprocating saw blade is within an acceptable range of the vertical tibial resection plane 104).

Referring again to FIG. 4, after performing the tibial resections, the surgeon may use the device 12 to confirm the surgical plan based on the tibial registration. In particular, the surgeon may assess joint alignment and balance using the user interface 58 and the joint balance graph 86 as described above. The surgeon may modify one or more parameters of the surgical plan (within constraints imposed by the resections already performed) as described above. The surgeon confirms the surgical plan when the surgical parameters of the surgical plan and the joint balance graph 86 are satisfactory.

Figure 9:
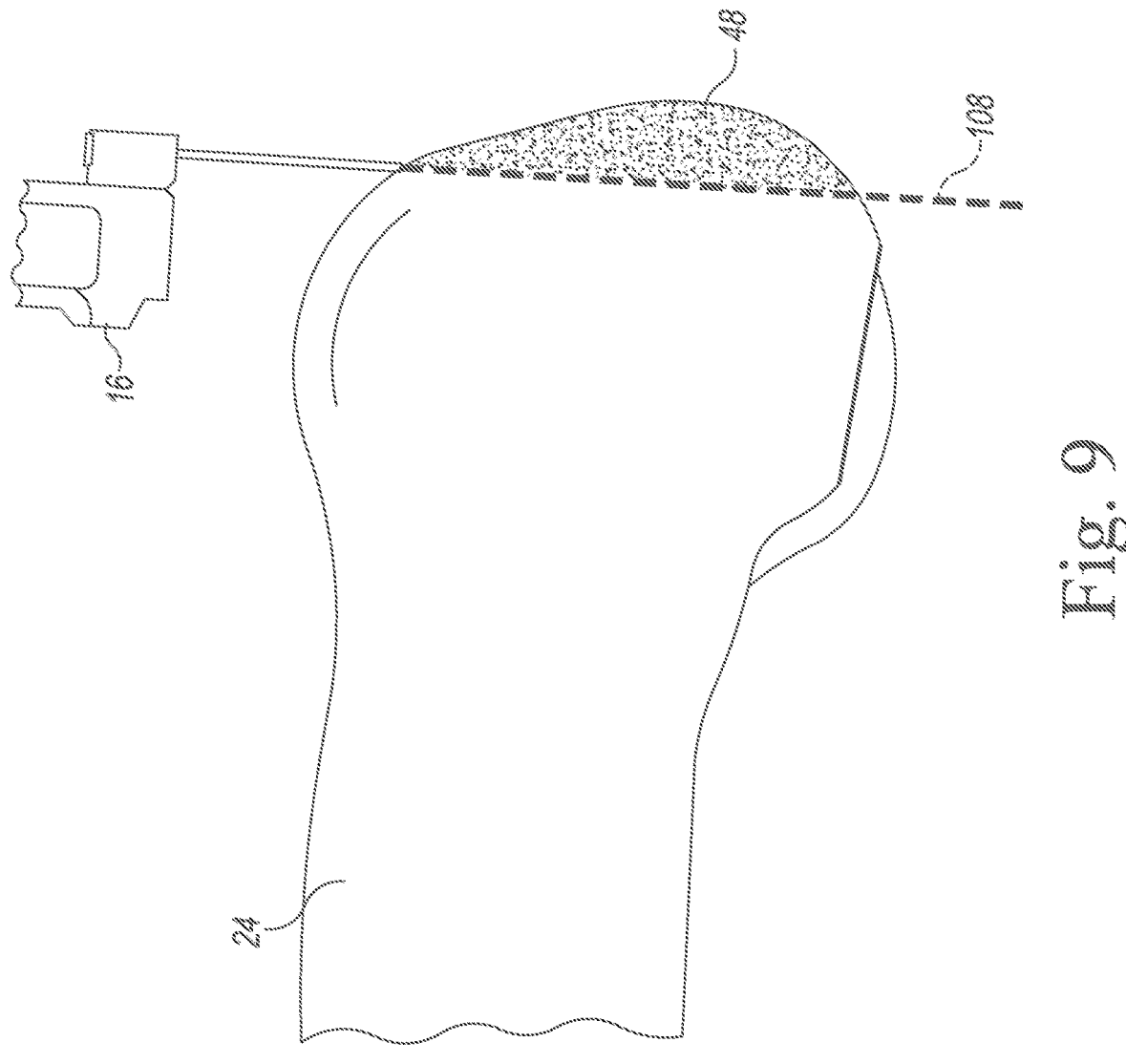
FIG. 9 is a perspective diagram illustrating a distal femoral resection performed during the orthopaedic surgical procedure.

Referring now to FIG. 9, after confirming the surgical plan, the surgeon uses the robotic surgery device 14 to perform a distal femoral resection in the illustrative embodi- ment. The robotic surgery device 14 positions the surgical saw 16 in a distal femoral resection plane 108. The distal femoral resection plane 108 is defined by the surgical plan described above. For example, the height and/or angle of the distal femoral resection plane 108 may be determined based on the femoral prosthesis flexion/extension angle 70 and/or other surgical parameters of the surgical plan. The robotic surgical system 14 supports the surgical saw 16 and may constrain movement of the surgical saw 16 within the distal femoral resection plane 108 while the surgeon uses the surgical saw 16 to perform the distal femoral resection.

After performing the distal resection, the surgeon may use the device 12 to verify accuracy of the distal resection. The surgeon places the tip 34 of the pointer 32 on the surgically prepared distal surface of the femur 24, and the device 12 captures the position of the pointer 32. The device 12 may display a representation of the relative locations of the tip 34 and the femur 24 and may indicate whether the tip 34 is positioned on the predetermined position of the distal resec- tion. For example, the display 22 may include a graphical representation of the relative locations of the tip 34 and the femur 24 and a numerical representation of the distance between the current location of the tip 34 and the planned distal resection.

Figure 10:
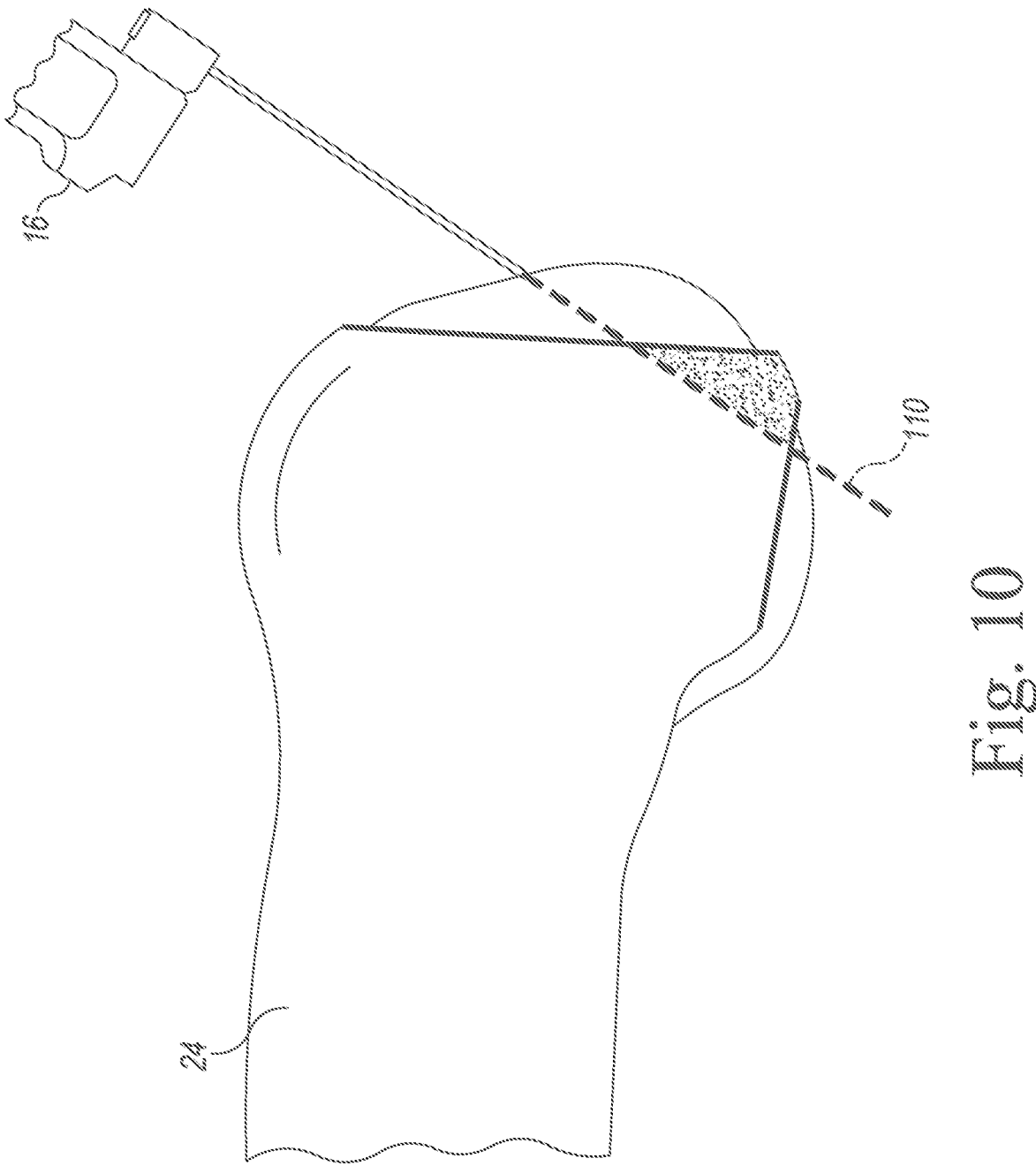
FIG. 10 is a perspective diagram illustrating a posterior chamfer femoral resection performed during the orthopaedic surgical procedure.

Referring now to FIG. 10, the surgeon also uses the robotic surgery device 14 to perform a posterior chamfer resection. The robotic surgery device 14 positions the sur- gical saw 16 in a posterior chamfer resection plane 110. The posterior chamfer resection plane 110 is defined by the surgical plan described above. The robotic surgical system 14 supports the surgical saw 16 and may constrain move- ment of the surgical saw 16 within the posterior chamfer resection plane 110 while the surgeon uses the surgical saw 16 to perform the posterior chamfer resection.

As described above, in some embodiments, the surgeon may perform a preliminary posterior femur resection that is some distance short of the posterior femoral resection height 64 defined in the surgical plan (e.g., to allow for greater refinement of the surgical plan after performing the later tibial registration). In those embodiments, the surgeon may adjust and otherwise confirm the surgical plan after acquir- ing additional data and/or performing additional resections as described above. The surgeon may perform the final posterior femur resection similar to as described above in connection with FIG. 5. In some embodiments, the device 12 may detect and notify the surgeon of a potential for creating a faceted cut on the femur so that the surgeon can modify the surgical plan as necessary or desired.

Figure 11:
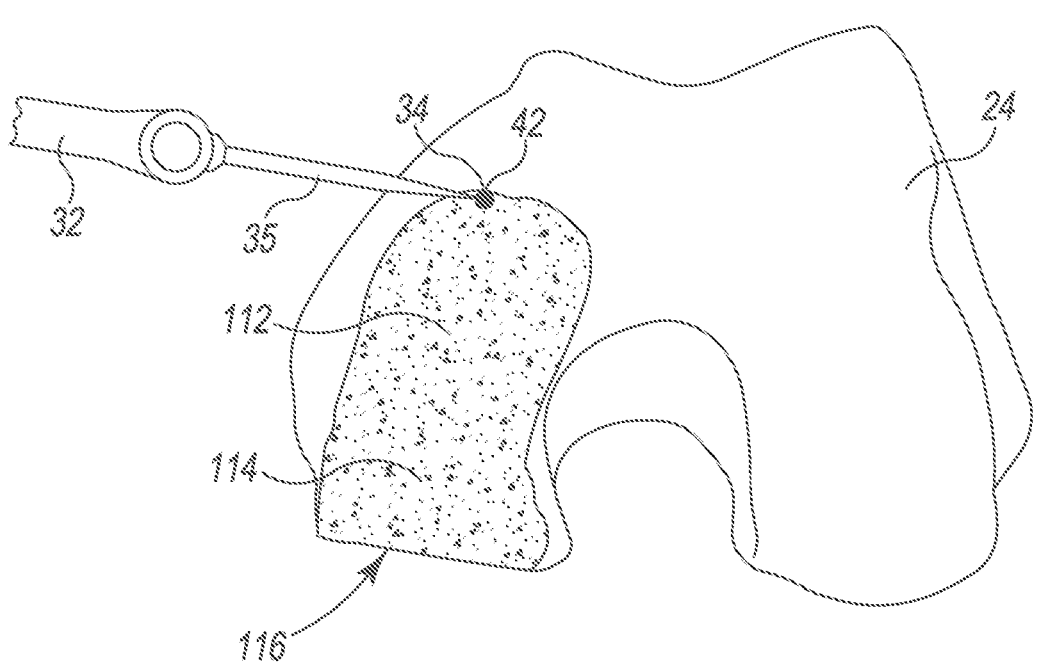
FIG. 11 is a perspective diagram illustrating surgical navigation of the patient's femur performed during the orthopaedic surgical procedure.

Referring now to FIG. 11, after performing the resections of the surgical plan, the surgeon uses the system 10 to navigate to the femoral anterior point 42. The surgeon places the tip 34 of the pointer 32 on a surgically prepared distal surface 112 of the femur 24, and the system 10 captures the position of the pointer 32. The device 12 may display a representation of the relative locations of the tip 34 and the femur 24, and may indicate whether the tip 34 is positioned on the predetermined position of anterior point 42. For example, the display 22 may include a graphical represen- tation of the relative locations of the tip 34 and the femur 24 and a numerical representation of the distance between the current location of the tip 34 and the planned anterior point 42. When the tip 34 is positioned at the anterior point 42, the surgeon marks the bone 24. The surgeon may use this mark to continue performing the orthopaedic surgical procedure using one or more manual instruments. For example, the surgeon may attach a femoral finishing block, cutting guide, jig, or other surgical alignment tool to the surgical prepared surface 112 using the marked point 42 as a reference. The surgeon may use that femoral finishing block to drill, ream, or otherwise prepare peg holes in the surgically prepared surface 112. Additionally or alternatively, the surgeon may use the system 10 to verify accuracy of the surgically prepared distal surface 112, a surgically prepared posterior chamfer surface 114, and/or a surgically prepared posterior surface 116 as described above.

Figure 12:
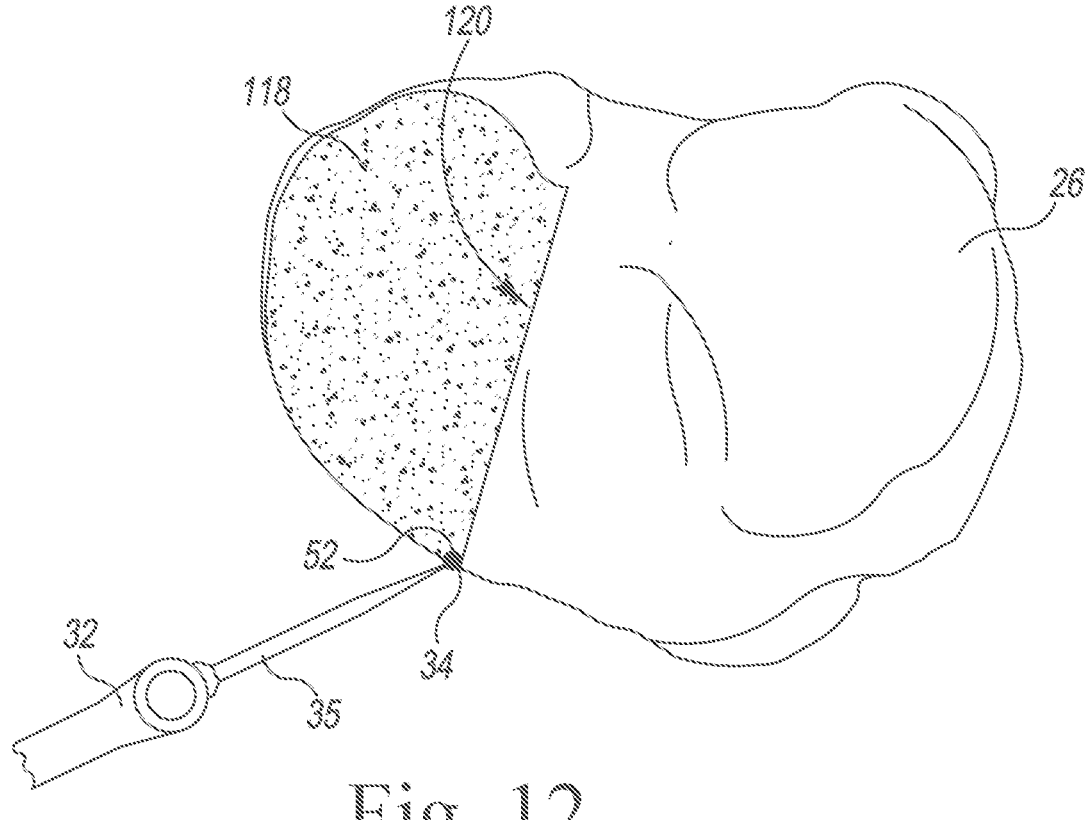
FIG. 12 is a perspective diagram illustrating surgical navigation of the patient's tibia performed during the orthopaedic surgical procedure.

Referring now to FIG. 12, after performing the posterior chamfer resection, the surgeon uses the system 10 to navigate to the tibial anterior point 52. The surgeon places the tip 34 of the pointer 32 on a surgically prepared tibial surface 118, and the system 10 captures the position of the pointer 32. The device 12 may display a representation of the relative locations of the tip 34 and the tibia 26, and may indicate whether the tip 34 is positioned on the predetermined position of the anterior point 52. For example, the display 22 may include a graphical representation of the relative locations of the tip 34 and the tibia 26 and a numerical representation of the distance between the current location of the tip 34 and the planned anterior point 52. When the tip 34 is positioned at the anterior point 52, the surgeon marks the bone 26. The surgeon may use this mark to continue performing the orthopaedic surgical procedure using one or more manual instruments. For example, the surgeon may attach a tibial template, cutting guide, jig, or other surgical alignment tool to the surgical prepared surface 118 using the marked point 52 as a reference. The surgeon may use that tibial template to drill, ream, broach, cut, or otherwise prepare a peg hole and a keel slot in the surgically prepared surface 118. Additionally or alternatively, the surgeon may use the system 10 to verify accuracy of the surgically prepared tibial surface 118 and/or a surgically prepared vertical cut surface 120 as described above.

After surgically preparing the femur 24 and the tibia 26 as described above, the surgeon completes the UKA surgical procedure. For instance, the surgeon may attach one or more trial prostheses to the femur 24 and the tibia 26. The surgeon may use the device 12 to assess leg alignment and balance as described above in connection with FIG. 4. The surgeon implants a final femoral prosthesis and a final tibial prosthesis, which may include or otherwise be coupled with a tibial insert. The surgeon may use the device 12 to assess final leg alignment and joint balance as described above in connection with FIG. 4.

While the illustrative embodiment shown in the drawings and described above utilizes a posterior femoral resection as the first resection, alternative embodiments may utilize a distal femoral resection as the first resection. In such embodiments, after performing the initial registration (as described above with reference to FIGS. 2-3) and developing a surgical plan based on that initial registration (as described above with reference to FIG. 4), the surgeon may proceed to use the robotic surgery device 14 to perform a distal femoral resection in substantially the same manner as described above with reference to FIG. 9. In some embodiments, the resection plane 108 may be positioned some distance short of a distal femoral resection height defined in the surgical plan. In those embodiments, the final distal femoral resection height of the surgical plan may be further adjusted before making a final cut on the distal femur. Performing a distal femoral resection (rather than a posterior femoral resection) as the first resection may be advantageous in some cases because it will permit later modification of the surgical plan to alter the rotation of the femoral prosthesis.

After performing a distal femoral resection as the first resection, the surgeon uses the pointer 32 to register or otherwise measure features of the patient's natural tibia 26, in substantially the same manner described above with reference to FIGS. 6 and 7. In particular, the surgeon may position the tip 34 of the pointer 32 on one or more locations of the patient's tibia 26 that were previously inaccessible due to tightness of the knee, but that are now accessible after performing the first femoral resection. In this embodiment, the surgeon may orient the knee joint in extension during this registration in order to maximize access to the posterior tibia. (By contrast, where the surgeon performs a posterior femoral resection as the first resection, the surgeon may orient the knee joint in flexion during this registration in order to maximize access to the posterior tibia.) After completing registration of the tibia, the surgeon may confirm the surgical plan (as described above), perform one or more tibial resections (as described above with reference to FIG. 8), perform a distal femoral resection (as described above with reference to FIG. 5), perform a posterior chamfer femoral resection (as described above with reference to FIG. 10), optionally perform a final distal femoral resection (as discussed above), and otherwise completes the UKA surgical procedure (as described above).

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A method for an orthopaedic surgical procedure, the method comprising:

performing, using a surgical navigation system, one or more initial measurements on a femur of a patient, a tibia of the patient, or both;

developing, using the surgical navigation system, a surgical plan for the orthopaedic surgical procedure based on the one or more initial measurements;

intraoperatively performing a first resection of the femur;

intraoperatively performing, using the surgical navigation system, one or more later measurements of the tibia that were inaccessible prior to the first resection of the femur;

intraoperatively confirming, using the surgical navigation system, the surgical plan based on the one or more later measurements of the tibia;

intraoperatively performing a tibial resection of the tibia based on a planned tibial resection plane of the surgical plan after confirming the surgical plan; and intraoperatively performing additional resections of the femur based on planned femoral resection planes of the surgical plan after confirming the surgical plan.

2. The method of claim 1, wherein the first resection is a posterior femoral resection.

3. The method of claim 1, wherein the first resection is a distal femoral resection.

4. The method of claim 1, wherein intraoperatively performing the one or more later measurements of the tibia comprises recording one or more posterior points of a compartment of the tibia.

5. The method of claim 4, wherein recording the one or more posterior points comprises recording a most-posterior point of the compartment of the tibia.

6. The method of claim 1, wherein intraoperatively performing the one or more later measurements of the tibia comprises recording a most-lateral or most-medial point of a compartment of the tibia.

7. The method of claim 1, wherein intraoperatively performing the one or more later measurements of the tibia comprises recording a natural slope of the tibia.

8. The method of claim 6, wherein recording the natural slope of the tibia comprises sensing a navigated pointer instrument of the surgical navigation system while an elongated body of the navigated pointer instrument is aligned with the natural slope of the tibia.

9. The method of claim 1, wherein intraoperatively performing the one or more later measurements of the tibia comprises sensing a navigated pointer instrument of the surgical navigation system while a tip of the navigated pointer instrument contacts a point on the tibia that was inaccessible to the navigated pointer instrument prior to the first resection of the femur.

10. The method of claim 1, wherein intraoperatively performing the one or more later measurements of the tibia comprises scanning a surface of the tibia with a laser scanner, a white light scanner, or a structured light scanner.

11. The method of claim 1, wherein intraoperatively performing the first resection of the femur comprises resecting the femur along a planned posterior femoral resection plane or a planned distal femoral resection plane of the surgical plan.

12. The method of claim 1, wherein:
   intraoperatively performing the first resection of the femur comprises resecting the femur along a preliminary plane that is either (i) posterior of a planned posterior femoral resection plane of the surgical plan or (ii) distal of a planned distal femoral resection plane of the surgical plan; and
   intraoperatively performing the additional resections of the femur based on planned femoral resection planes of the surgical plan after intraoperatively confirming the surgical plan comprises resecting the femur along the planned posterior femoral resection plane of the surgical plan and resecting the femur along the planned distal femoral resection plane of the surgical plan.

13. The method of claim 1, wherein intraoperatively confirming the surgical plan based on the one or more later measurements of the tibia comprises intraoperatively modifying the surgical plan based on the one or more later measurements of the tibia.

14. The method of claim 13, wherein:
   the surgical plan developed prior to intraoperatively performing the one or more later measurements of the tibia includes the planned tibial resection plane; and intraoperatively modifying the surgical plan based on the one or more later measurements of the tibia comprises modifying the planned tibial resection plane.

15. The method of claim 13, wherein:
   the surgical plan developed prior to intraoperatively performing the one or more later measurements of the tibia does not include the planned tibial resection plane; and
   intraoperatively modifying the surgical plan based on the one or more later measurements of the tibia comprises adding the planned tibial resection plane to the surgical plan.

16. The method of claim 13, wherein intraoperatively modifying the surgical plan based on the one or more later measurements of the tibia comprises setting the planned tibial resection plane to mimic a natural slope of the tibia.

17. The method of claim 16, wherein intraoperatively modifying the surgical plan further comprises setting the planned femoral resection planes to mimic a natural joint space in flexion and to achieve a balanced joint space in extension.

18. The method of claim 1, wherein intraoperatively performing a tibial resection after confirming the surgical plan comprises (i) performing a horizontal tibial resection of the tibia based on a planned horizontal tibial resection plane of the surgical plan and (ii) performing a vertical tibial resection of the tibia based on a planned vertical tibial resection plane of the surgical plan.

19. The method of claim 1, wherein intraoperatively performing the first resection of the femur, intraoperatively performing the tibial resection of the tibia, and intraoperatively performing the additional resections of the femur each comprises operating a robotic assisted surgery device in communication with the surgical navigation system, wherein movement of the robotic assisted surgery device is constrained according to surgical plan.

20. A method for an orthopaedic surgical procedure, the method comprising:
   performing, using a surgical navigation system, one or more femoral measurements on a femur of a patient;
   developing, using the surgical navigation system, a surgical plan for the orthopaedic surgical procedure based on the one or more femoral measurements;
   intraoperatively performing at least one resection of the femur based on the surgical plan;
   intraoperatively performing, using the surgical navigation system after performing the at least one resection of the femur, one or more tibial measurements of one or more posterior points on a tibia of the patient;
   intraoperatively confirming, using the surgical navigation system, the surgical plan based on the one or more tibial measurements; and
   intraoperatively performing a tibial resection of the tibia based on the surgical plan after confirming the surgical plan.

* * * * *